(12) United States Patent
Kelly et al.

(10) Patent No.: US 10,176,612 B2
(45) Date of Patent: Jan. 8, 2019

(54) SYSTEM AND METHOD FOR RETRIEVAL OF SIMILAR FINDINGS FROM A HYBRID IMAGE DATASET

(71) Applicant: Siemens Medical Solutions USA, Inc., Malvern, PA (US)

(72) Inventors: Matthew David Kelly, Oxford (GB); David Schottlander, Wickford (GB); Ludovic Sibille, Didcot (FR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 192 days.

(21) Appl. No.: 14/751,708

(22) Filed: Jun. 26, 2015

(65) Prior Publication Data

US 2015/0379365 A1    Dec. 31, 2015

(30) Foreign Application Priority Data

Jun. 27, 2014    (GB) .................................. 1411535.6

(51) Int. Cl.
| | |
|---|---|
| *G06K 9/00* | (2006.01) |
| *G06T 11/60* | (2006.01) |
| *G06T 7/00* | (2017.01) |
| *G06K 9/46* | (2006.01) |
| *G06K 9/62* | (2006.01) |
| *G06F 19/00* | (2018.01) |
| *G16H 50/70* | (2018.01) |

(52) U.S. Cl.
CPC .............. *G06T 11/60* (2013.01); *G06F 19/00* (2013.01); *G06F 19/321* (2013.01); *G06K 9/4676* (2013.01); *G06K 9/6212* (2013.01); *G06T 7/0012* (2013.01); *G16H 50/70* (2018.01); *G06K 2209/05* (2013.01); *G06T 2207/10081* (2013.01); *G06T 2207/10084* (2013.01); *G06T 2207/10088* (2013.01); *G06T 2207/10104* (2013.01); *G06T 2207/10108* (2013.01); *G06T 2207/30096* (2013.01)

(58) Field of Classification Search
CPC . A61B 6/463; A61B 8/483; A61B 2090/3966; A61B 6/5247; A61B 1/0005; G06T 7/0012; G06T 2207/10088; G06T 2207/30004; G06T 2207/10072; G06T 2207/10081; G06T 2207/10121; G06T 2207/10084; G06T 2207/20221; G06F 19/321; G01T 1/2978; G01T 1/1603; G06K 2009/4666; G06K 9/46; G06K 9/00536; G06K 9/6255
See application file for complete search history.

(56) References Cited

U.S. PATENT DOCUMENTS

2005/0187916 A1* 8/2005 Levin ........................ G06F 7/02
2007/0019846 A1* 1/2007 Bullitt .................. G06T 7/0014
382/128

(Continued)

FOREIGN PATENT DOCUMENTS

WO    WO-00/70528 A2    11/2000

*Primary Examiner* — Vu Le
*Assistant Examiner* — Guillermo M Rivera-Martinez
(74) *Attorney, Agent, or Firm* — Schiff Hardin LLP

(57) ABSTRACT

In a method for retrieval of similar findings from a hybrid image dataset, a database of hotspots is prepared, wherein the hotspots are identified by binary strings encoding descriptors, and identify binary strings stored in the database are identified that resemble a new binary string.

14 Claims, 1 Drawing Sheet

(56) References Cited

U.S. PATENT DOCUMENTS

| | | | |
|---|---|---|---|
| 2007/0081712 A1* | 4/2007 | Huang | G06T 7/174 |
| | | | 382/128 |
| 2007/0092864 A1* | 4/2007 | Reinhardt | G06T 7/0012 |
| | | | 435/4 |
| 2007/0167784 A1* | 7/2007 | Shekhar | A61B 6/032 |
| | | | 600/443 |
| 2007/0287906 A1 | 12/2007 | Kadir et al. | |
| 2008/0292194 A1* | 11/2008 | Schmidt | G06T 7/0012 |
| | | | 382/217 |
| 2009/0105583 A1 | 4/2009 | Martin et al. | |
| 2010/0098306 A1* | 4/2010 | Madabhushi | G06K 9/0014 |
| | | | 382/128 |
| 2010/0172567 A1* | 7/2010 | Prokoski | A61B 5/0064 |
| | | | 382/132 |
| 2011/0188706 A1* | 8/2011 | Zhou | G06K 9/00 |
| | | | 382/103 |
| 2014/0153806 A1 | 6/2014 | Glielmi et al. | |
| 2016/0004412 A1* | 1/2016 | Meyer | G06F 3/0484 |
| | | | 345/581 |

* cited by examiner

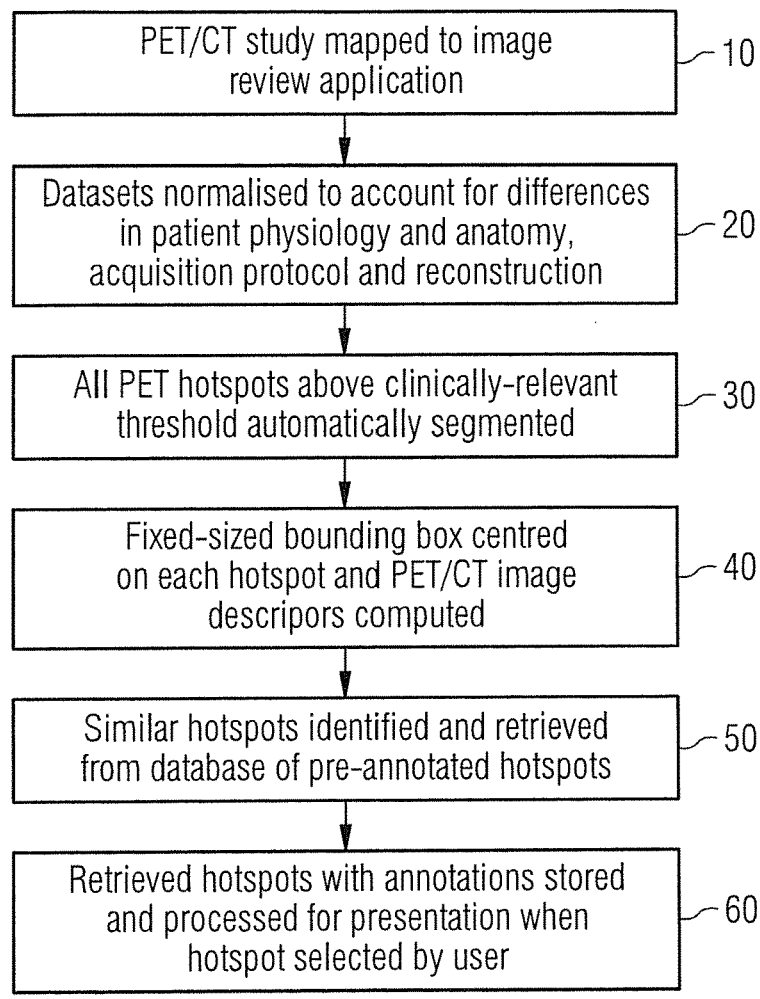
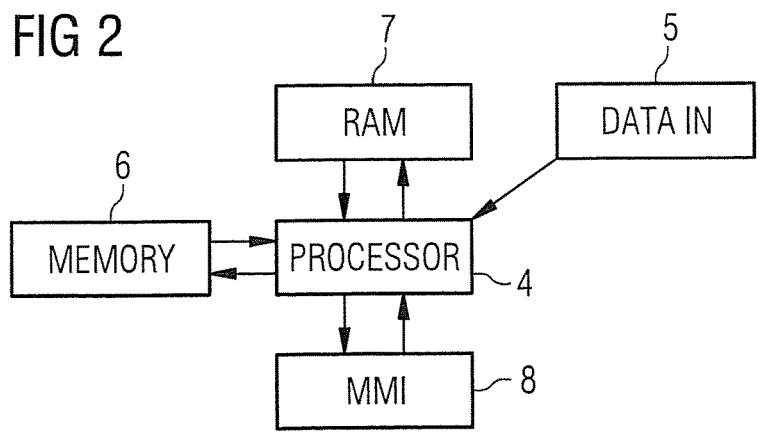

SYSTEM AND METHOD FOR RETRIEVAL OF SIMILAR FINDINGS FROM A HYBRID IMAGE DATASET

BACKGROUND OF THE INVENTION

Field of the Invention

The present invention relates to methods and apparatus for assisting in interpretation of images, particularly patient medical images, and particularly hybrid anatomical-functional patient medical image datasets.

Description of the Prior Art

It is well known that medical image data can be captured in multiple modalities and the image data from these modalities aligned to assist with detection and interpretation of multiple features. Typically, an anatomical imaging modality such as MRI or CT provides data on the position, size and shape of organs, while a functional imaging modality such as PET or SPECT provides information on the state of the organs, for example indicating lesions by their increased uptake of an introduced tracer. As images in these differing modalities must be captured by correspondingly differing equipment, alignment must be carried out to ensure correct registration between the sets of image data, even if the two sets of image data were captured at the same time on a multimodality imaging equipment. Alignment methods are known in the art, and do not form part of the present invention.

In a typical scenario, a patient is imaged several times over an extended period of time, lasting several months. The present invention is directed to methods and systems to aid a user in retrieving similar findings from stored image records when presented with a new image dataset.

A finding in a multi-modality patient medical image dataset is typically defined by its intensity, appearance and location, as well as the patient's clinical history and referring indication, that is, the subject of a question that a referring physician (e.g., oncologist) wants answering. For example, for a patient with lung cancer, the referring indication may be the stage of the cancer, or the efficacy of the treatment.

As part of a clinical read, a user will classify their findings based on such features, in combination with any other findings in the image and non-image features, such as patient history, histopathology. Retrieval and presentation of similar lesions which have already been classified may aid a user in assessment of lesions in a newly-presented image dataset. Further information which may be available regarding these similar lesions, such as treatment strategy and patient response, may also be useful to a user in planning patient management decisions.

In another application, retrieval of similar stored information regarding similar lesions from earlier datasets may be useful to a user in determining an appropriate label for a selected lesion. For example, a newly-presented image representing a lesion may be compared to earlier representations of benign and malignant lesions to assist a user in classification or annotation of the newly-presented lesion.

In order to be useful in a medical imaging environment, the identification and retrieval of records of similar lesions must occur rapidly, while the information they provide should maintain high quality and pertinence to the case.

Some attempts have been made in the past to provide content-based image retrieval (CBIR) systems, but the complexity of the task and the volume of data involved have made this a technically challenging task. Known CBIR systems typically take as an input a user-specified image that includes a feature of interest. Quantitative descriptors are then computed for the image and are tested for similarity against a pre-processed database of images. Such image-intensity descriptors can be computed quickly, but the retrieval of identified image data of matched lesions is typically time-consuming due to the quantity of image data involved, and the transmission speeds of networks carrying the data.

The image-intensity descriptors used by known CBIR systems are, in themselves, unlikely to encode additional clinically-important properties, such as the anatomical location of the lesion, and its relative position to organ boundaries. Ex-5 traction of such properties may be performed by known means and methods, such as detecting lesion position relative to anatomical landmarks and lesion segmentation. A processing time of the image data will be lengthened by the extraction step. Pre-computation would be required to meet performance 10 requirements.

SUMMARY OF THE INVENTION

An object of the present invention is to address these difficulties and accordingly provides methods and systems as defined in the appended claims.

The above object is achieved in accordance with the present invention by a method and system for retrieval of similar findings from a hybrid image dataset, a database of hotspots is prepared, wherein the hotspots are identified by binary strings encoding descriptors, and wherein binary strings stored in the database that resemble a new binary string are identified.

BRIEF DESCRIPTION OF THE DRAWINGS

FIG. 1 is a flowchart of an exemplary method according to the present invention.

FIG. 2 schematically illustrates a computer-implemented system according to an embodiment of the present invention.

DESCRIPTION OF THE PREFERRED EMBODIMENTS

The present invention provides systems and methods for rapidly identifying and retrieving stored image data and associated information for use in interpreting image data.

The present invention includes the steps of assessing functional image data to pre-process likely regions of clinical significance, and ensuring that data for similar lesions is ready for presentation to a user when the user wishes to interpret a new image dataset. In the example method represented by FIG. 1, step 10 requires a multi-modality image dataset, such as a PET/CT study, to be mapped to prepare the image dataset for pre-processing tasks.

For example, "mapping" may refer to an act of assigning a patient dataset to a specific work flow for reading. Typically, a set of "rules" are defined to automatically map patient data with certain properties to a certain workflow.

Typically, although not necessarily, the multi-modality dataset will include an anatomical modality (e.g. CT or MRI) and a functional modality (e.g. PET of SPECT).

Pre-processing tasks may then be carried out.

Next, at step 20, the mapped image datasets are normalized. That is, they are processed by methods known in themselves to allow comparison with datasets acquired with different scanners and/or different reconstruction protocols; differences in patient physiology and anatomy. For the latter, a landmark-based registration process may be used.

At step 30, local maxima—which may be colloquially referred to as "hotspots"—are detected, being regions with an intensity above a certain clinically-relevant threshold value in the functional image. This may be achieved by known methods. These are segmented into regions of interest, preferably by a known automated step.

Next, at step 40, for each hotspot, a bounding box is defined in the image datasets, containing the hotspot and preferably centered on the location of the hotspot. An equivalent bounding box, that is, one of the same size and shape, is then positioned in the same location in the co-registered anatomical image such as CT or MRI. The image region defined by the bounding box is processed to calculate image-intensity descriptors for the functional image data and the corresponding anatomical image data. The bounding boxes may be of a fixed size or may be of variable size, adapted to suit the size and shape of the identified hotspot.

Preferably, the location of the hotspot is defined relative to a set of anatomical landmarks. Preferably, the anatomical landmarks are automatically determined and the position is preferably defined by a set of vector displacements from those anatomical landmarks.

Preferably, the location of the hotspot, either inside or outside a set of organ segmentations is computed. The organ segmentation may be automatically computed using a conventional organ segmentation technology.

Once such localization descriptors and image intensity descriptors have been calculated for the hotspot, these are encoded into a binary string. A binary string may be transmitted rapidly, and may be processed rapidly, unlike the case of transmitting complete image data.

Features determined from the image data within the bounding box may then be matched against features derived from a pre-processed image database, using the same-sized bounding box.

At step 50, similar hotspots are identified and retrieved from a pre-stored database of pre-annotated hotspots. This is made simple by the encoding of localization descriptors and image intensity descriptors into a binary string. The pre-stored database may store comparable binary strings, encoding localization descriptors and image intensity descriptors of previously-processed hotspots, and the comparison with the new hotspot may be carried out using a binary string similarity algorithm.

Hotspots identified as being similar, in this example based on the comparison of the binary strings encoding localization descriptors and image intensity descriptors of the new hotspot and the previously-processed hotspots, are extracted from the database. Preferably, the database contains further information about the hotspots, such as clinical annotations.

At step 60, the retrieved hotspots are stored and processed for presentation to a user, along with any accompanying annotations. In response to user selection of a particular hotspot, corresponding retrieved hotspots are presented to the user for comparison, along with the selected hotspot. Any accompanying clinical annotations or other information may also be presented.

While the system is simplified by use of a fixed-size bounding box, such as a 3 cm cube, a 5 cm cube or a 7 cm cube, other shaped bounding boxes may be employed depending on the size and shape of the hotspot in question, or the segmentation or body location involved.

The image-intensity descriptors used may be any suitable known functions, and may for example be a histogram of oriented gradients, Gabor descriptors, Gray level co-occurrence matrices. These may be calculated for any given hotspot for the purpose of retrieval of similar hotspots from the database.

The present invention accordingly provides a system and apparatus for efficient retrieval of similar findings for a hybrid anatomical-functional image dataset.

In an embodiment, the invention includes the further step of normalizing the image datasets to account for differences not attributable to the clinical condition of the patient, for example differences in physiology, scanner physics, acquisition protocol and reconstruction and anatomy.

The method may then comprise computing all local image intensity maxima in the functional image above a locally-specified intensity threshold and encoding each local image intensity maximum as a binary string. The binary string may represent image features such as localization descriptors and image intensity descriptors, and/or clinically relevant features of the hotspot. Such binary string may then be compared with similarly-computed strings from a database of normalized annotated hybrid datasets using a string similarity measure.

A number of binary strings exhibiting the greatest similarity according to the similarity measure are then returned by the database. The number may be a predetermined number, or it may comprise all binary strings exhibiting a similarity measure above a certain threshold.

Clinically-relevant features represented in the binary string may include image-intensity-derived descriptors from the functional image, image-intensity-derived descriptors from the anatomical image, distances from pre-computed anatomical landmarks such as the carina, information as to the proximity of, or inclusion within, a segmented organ such as the liver.

In a preferred embodiment, annotated datasets corresponding to identify binary strings are retrieved prior to the user opening a case for reading.

In certain embodiments, annotations related to datasets corresponding to identify binary strings are presented to the user as possible annotations for the selected finding.

Preferably, the user is able to review the datasets corresponding to identify binary strings as associated with the proposed annotations.

Referring to FIG. 2, embodiments of the invention may be conveniently realized as a computer system suitably programmed with instructions for carrying out the steps of the methods according to the invention.

For example, a central processing unit 4 is able to receive data representative of medical scan data via a port 5 which could be a reader for portable data storage media (e.g. CD-ROM), a direct link with the apparatus such as a medical scanner (not shown) or a connection to a network.

For example, in an embodiment, the processor performs: normalizing the functional image data within the hybrid image dataset; identifying local maxima in the functional image; segmenting regions of local maxima into regions of interest; defining a bounding box in the image datasets of the hybrid image dataset; processing the image region of the hybrid image dataset corresponding to the location of the bounding box, to calculate image-intensity descriptors for the image region; encoding localization descriptors and image intensity descriptors into a new binary string; comparing the new binary string to a number of binary strings stored in the database; and identifying binary strings stored in the database which resemble the new binary string.

Software applications loaded on memory 6 are executed to process the image data in random access memory 7.

A Man-Machine interface 8 typically includes a keyboard/mouse/screen combination that allows user input such as initiation of applications and a screen on which the results of executing the applications are displayed.

While the present invention has been particularly explained with reference to hybrid image datasets, comprising aligned—co-registered—image datasets in at least one functional modality and at least one anatomical modality, the present invention may be applied to datasets that include image datasets from only a single modality or a number of anatomical modalities only, or a number of functional modalities only.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for retrieval of similar findings from a hybrid image dataset, comprising:
   in a processor, preparing a database of local maxima, identified by binary strings encoding descriptors;
   providing said processor with functional image data representing a functional image of a subject, and anatomical image data representing am anatomical image of the subject, said functional image containing at least one local maximum having an intensity that is above a clinically-relevant threshold value;
   in said processor, aligning said functional image data and said anatomical image data to form the hybrid image dataset;
   in said processor, normalizing the functional image data within the hybrid image dataset;
   in said processor, identifying each local maximum in said functional image data;
   in said processor, segmenting regions of the functional image, with each region of interest containing a respective local maximum in order to designate regions of interest in said functional image;
   in said processor, defining a bounding box, having a size and shape, around each region of interest in said functional image and then defining an equivalent bounding box, having the same size and shape, for an image region in the anatomical image data aligned with the functional image data in the hybrid image dataset;
   in said processor, processing each image region of the hybrid image dataset, corresponding to the location of the equivalent bounding box, to calculate descriptors for the image region bounded by the equivalent bounding box in the hybrid image dataset;
   in said processor, encoding descriptors relating to the processed image region into a new binary string;
   in said processor, comparing the new binary string to a number of binary, strings stored in the database; and
   in said processor, identifying binary strings stored in the database which resemble the new binary string, and making the new binary string available in electronic format output of the processor for retrieval of said similar findings.

2. A method according to claim 1, wherein the encoded descriptors comprise image intensity descriptors.

3. A method according to claim 2, comprising identifying local maxima by identifying regions with an intensity above a certain clinically-relevant threshold in the functional image.

4. A method according to claim 1, wherein the encoded descriptors comprise localization descriptors.

5. A method according to claim 4 comprising defining localization descriptors relative to a set of anatomical landmarks.

6. A method according to claim 4 wherein defining the localization descriptors as a set of vector displacements from the anatomical landmarks.

7. A method according to claim 1 comprising displaying image regions corresponding to the identified binary strings to a user.

8. A method according to claim 1 comprising using the binary strings stored within the database to encode descriptors relating to pre-processed image regions defined by a bounding box of the same dimension as the bounding box defining the image region used to define the new binary string.

9. A method according to claim 1 comprising evaluating which binary strings are similar based on the encoded descriptors.

10. A method according to claim 1 comprising storing image regions corresponding to the identified binary strings, and processing the stored image regions for presentation to a user.

11. A method according to claim 10 comprising, in response to user selection of a local maximum, retrieving image regions corresponding to the identified binary strings and presented to the user for comparison, along with image region corresponding to the selected local maximum.

12. A method according to claim 1, wherein the database further contains annotations linked with image regions, and displaying said annotations to a user together with the image region.

13. An apparatus for retrieval of similar findings from a hybrid image dataset, comprising:
   a processor in communication with a display device;
   said processor being provided with functional image data representing a functional image of a subject, and anatomical image data representing am anatomical image of the subject, said functional image containing at least one local maximum having an intensity that is above a clinically-relevant threshold value;
   said processor being configured to align said functional image data and said anatomical image data to form the hybrid image dataset;
   said processor being configured to normalize the functional image data within the hybrid image dataset;
   said processor being configured to identify each local maximum in said functional image data;
   said processor being configured to segment regions of the functional image in order to designate regions of interest in said functional image, with each region of interest containing a respective local maximum;
   said processor being configured to define a bounding box, having a size and shape, around each region of interest in said functional image and then to define an equivalent bounding box, having the same size and shape, for an image region in the anatomical image data aligned with the functional image data in the hybrid image dataset;
   said processor being configured to process the image region of the hybrid image dataset corresponding to the location of the equivalent bounding box, to calculate image-intensity descriptors and localization descriptors for the image region bounded by the equivalent bounding box in the hybrid image dataset;
   said processor being configured to encode the localization descriptors and image intensity descriptors for the image region into a new binary string;

said processor being configured to compare the new binary string to a number of binary strings stored in the database and identify binary strings stored in a database of local maxima which resemble the new binary string; and said processor being configured to cause the multi-fused image of the regions to be displayed at said display device.

14. A non-transitory, computer-readable data storage medium encoded with programming instructions, said storage medium being loaded into a processor that is in communication with a display device, and said programming instructions causing said processor to:

receive functional image data representing a functional image of a subject, and anatomical image data representing am anatomical image of the subject;

align said functional image data and said anatomical image data to form the hybrid image dataset, said functional image containing at least one local maximum having an intensity that is above a clinically-relevant threshold value;

normalize the functional image data within the hybrid image dataset;

identify each local maximum in said functional image data;

segment regions of the functional image data in order to designate regions of interest in said functional image data, with each region of interest containing a respective local maximum;

define a bounding box, having a size and shape, around each region of interest in said functional image data then define an equivalent bounding box, having the same size and shape, for an image region in the anatomical image data aligned with the functional image data in the hybrid image dataset;

process the image region of the hybrid image dataset corresponding to the location of the equivalent bounding box, to calculate image-intensity descriptors and localization descriptors for the image region bounded by the equivalent bounding box in the hybrid image dataset;

encode the localization descriptors and image intensity descriptors for the image region into a new binary string;

compare the new binary string to a number of binary strings stored in the database and identify binary strings stored in a database of local maxima which resemble the new binary string; and cause the multi-fused image of the regions to be displayed at said display device.

* * * * *